(12) United States Patent
Wyatt

(10) Patent No.: US 6,392,962 B1
(45) Date of Patent: May 21, 2002

(54) METHOD OF SLEEP TIME MEASUREMENT

(75) Inventor: Patrick Wyatt, Monterey, CA (US)

(73) Assignee: RMP, Inc., West Palm Beach, FL (US)

( * ) Notice: Subject to any disclaimer, the term of this patent is extended or adjusted under 35 U.S.C. 154(b) by 0 days.

(21) Appl. No.: 08/444,242

(22) Filed: May 18, 1995

(51) Int. Cl.[7] .......................... G04F 10/00; G04F 8/00; A61B 5/04

(52) U.S. Cl. ...................... 368/107; 368/110; 368/113; 600/382; 600/384

(58) Field of Search .............................. 368/9, 10, 28, 368/29, 69–70, 107–113, 278; 200/DIG. 2, 52 R; 128/774, 782; 340/573, 575; 600/372, 382, 384, 553

(56) References Cited

U.S. PATENT DOCUMENTS

| | | | |
|---|---|---|---|
| 450,966 A | 4/1891 | Matthews | |
| 589,672 A | 9/1897 | Schumacher et al. | |
| 1,046,225 A | * 12/1912 | Schindler | 200/DIG. 2 |
| 1,223,778 A | * 4/1917 | Ericson | 368/110 |
| 1,402,609 A | * 1/1922 | Hodous | 200/DIG. 2 |
| 2,111,193 A | * 3/1938 | Poole | 368/110 |
| 2,486,591 A | 11/1949 | Ferrante | |
| 3,158,987 A | 12/1964 | Hamilton | |
| 3,209,529 A | * 10/1965 | Hetzel | 368/110 |
| 3,226,501 A | 12/1965 | Seserman | |
| 3,548,812 A | 12/1970 | Palne | |
| 3,700,835 A | 10/1972 | Rackson | |
| 3,723,675 A | 3/1973 | Richey | |
| 3,944,843 A | 3/1976 | Vaz Martins | |
| 4,059,830 A | 11/1977 | Threadgill | |
| 4,069,659 A | 1/1978 | Harris et al. | |
| 4,396,296 A | 8/1983 | Stodden | |
| 4,493,043 A | * 1/1985 | Forbath | 364/569 |
| 4,505,595 A | 3/1985 | Rose et al. | |
| 4,537,514 A | 8/1985 | Moriya | |
| 4,652,141 A | 3/1987 | Arai | |
| 4,681,462 A | 7/1987 | Lloyd | |
| 4,748,601 A | * 5/1988 | Reidt et al. | 368/10 |
| 4,797,864 A | 1/1989 | Stano et al. | |
| 4,912,687 A | * 3/1990 | Treeby | 368/10 |
| 4,993,004 A | 2/1991 | Loizeaux | |
| 4,999,772 A | 3/1991 | Bowman et al. | |
| 5,088,072 A | 2/1992 | Fitzmorris | |
| 5,124,960 A | 6/1992 | Miller et al. | |
| 5,377,170 A | 12/1994 | Blaylock et al. | |
| 5,479,939 A | 1/1996 | Ogino | |
| 5,481,506 A | 1/1996 | Kita | |
| 5,520,176 A | 5/1996 | Cohen | |

* cited by examiner

Primary Examiner—Vit Miska
(74) Attorney, Agent, or Firm—Akerman, Senterfitt & Edison, P.A.

(57) ABSTRACT

A method to aid the treatment of sleeping disorders that are aggravated by an insomniac's underestimation of total sleep time and sleep efficiency, and overestimation of time necessary to fall asleep. The method includes an observation of the beginning of rest time and self-actuated measurement of the time necessary to fall asleep. The insomniac is made aware of the elapsed wake time and total sleep time upon wakening by further observing the time of awaking and the elapsed wake time as recorded on a wrist watch or other device. The apparatus can include a wrist mounted timer with a hand mounted actuator that stops timing when the insomniac falls asleep and disengages contact with the actuator.

18 Claims, 4 Drawing Sheets

| DATE | REST START TIME | SLEEP START TIME | AWAKE TIME | WAKE LAPSE TIME | TOTAL SLEEP TIME |
|------|-----------------|------------------|------------|-----------------|------------------|
|      |                 |                  |            |                 |                  |
|      |                 |                  |            |                 |                  |
|      |                 |                  |            |                 |                  |
|      |                 |                  |            |                 |                  |
|      |                 |                  |            |                 |                  |
|      |                 |                  |            |                 |                  |
|      |                 |                  |            |                 |                  |
|      |                 |                  |            |                 |                  |
|      |                 |                  |            |                 |                  |

METHOD OF SLEEP TIME MEASUREMENT

FIELD OF THE INVENTION

The present invention relates to a method and an apparatus for aiding the treatment of sleeping disorders that are aggravated by an insomniac's underestimation of total sleep time and sleep efficiency and overestimation of time necessary to fall asleep.

BACKGROUND OF THE INVENTION

Statistics indicate that sleeping disorders such as insomnia plague a significant percentage of the worlds population. People with insomnia in the United States alone number in the millions. Although there are several types or classifications of insomnia or similar sleeping disorders and a variety of possible causes, many theories suggest that insomniacs are generally either physiologically or cognitively hyperaroused relative to normal sleepers. In essence, many clinical tests and studies indicate that a substantial subset of people who suffer from insomnia unintentionally promote their condition by the anxiety resulting from their knowledge or misconception that they cannot readily fall asleep. It has been demonstrated that insomniacs generally underestimate their total sleep time and, more particularly, overestimate the amount of time necessary for them to fall asleep. As a result, the insomniac's problem is perpetuated and causes the insomniac to feel tired the next day.

Common methods of treating insomnia involve the use of prescription drugs or sleep training exercises, or both. For many reasons, a successful sleep training method would be preferred over drug therapy. Thus, a method of sleep training that allows the insomniac to make accurate determinations of sleep onset and total sleep time could contribute to the successful reduction or cure of an individual's insomnia.

Chronic insomnia is a distressing complaint that affects a significant percentage of the world's population; 35 to 40 million in the United States alone. Chronic insomnia is believed to be a problem for 15 to 30 percent of the adult population and close to 65 percent for some special groups, such as shift workers and psychiatric patients. Prevalence rates are fairly similar among the countries where insomnia has been studied: England, Finland, Israel and Italy. The number of advertisements for hypnotic drugs in the scientific journals give some idea of the importance of this disorder as a medical problem.

Three general types of insomnia have been described: initial, or sleep onset; intermittent, or sleep maintenance; and terminal, or early morning awakening. Several studies suggest that insomniacs are either physiologically or cognitively hyperaroused relative to normal sleepers. Individuals who are highly aroused may experience difficulty in falling asleep or may awaken frequently at night because sleep is associated with low levels of autonomic arousal. Data from two separate studies support the hypothesis that physiological arousal or anxiety is an etiological factor in insomnia. Insomniacs also seem to be characterized by neuroticism, anxiety, or worry. The results of a complete evaluation of nearly 8000 patients in the Sleep Disorders Clinics (ASDC) across the United States support the conventional hypothesis that insomnia is caused by depression or stress. In essence, multiple clinical tests and studies indicate that many people who suffer from insomnia unintentionally promote their condition by anxiety resulting from their knowledge that they cannot readily fall asleep. A significant direct correlation has been found between the Manifest Anxiety Scale score and 1) time required to fall asleep, 2) number of times awake, 3) time required to go back to sleep and 4) report of sleep difficulties. Corresponding daytime complaints typically include fatigue, sleepiness, poor performance, aching muscles, anxiety and loss of concentration and memory. Chronic insomniacs are two and one-half times as likely as non-insomniacs to report vehicle accidents in which fatigue was a factor. One study presented evidence that the complaint of insomnia is an important mortality risk factor. Similarly, clinical experiences support two hypotheses: 1) poor sleep causes drowsiness, poor health and, hence, poor performance, or 2) the complaint of insomnia indicates a person with chronic psychological problems that extend beyond sleep.

Well over half of any large population of individuals who complain of insomnia are likely to be using one or more sedative drugs on a daily basis. Although only five percent of insomniacs actually have visited a health professional for their sleep problems, 28 percent use alcohol, 29 percent self-administer over-the-counter medications and 12 percent use both to try to get to sleep. The estimated cost for retail prescriptions of hypnotics in 1970 was $170 million and has increased significantly since that time. In 1991, for example, three sleeping pills, Halcion, Restoril, and Dalmane accounted for nearly 11 million prescriptions written.

Many hypnotic drugs are ineffective and may cause sleep alterations, especially if consumed in excessive doses over long periods. One study found that initially the following drugs: chloral hydrate, ethcloruznol, glutethimide, methaqualone, methaqualone HCl and secobarbital were moderately to markedly effective in inducing or maintaining sleep, or both. The study also found, however, that, at the end of a two week period of drug administration, a loss of effectiveness for sleep induction or maintenance, or both, had developed with all these drugs. It is at this danger point where patients begin to increase their dosage or use to try to maintain the same effect. Consequently, the widespread use of hypnotic medication has also made accidental overdosage in people using or abusing these drugs a substantial health hazard. Where drugs are correctly administered, withdrawal of rapidly eliminated benzodiazepine hypnotics can lead to a condition called rebound insomnia. With ultrashort half-life drugs, early morning insomnia, another withdrawal phenomenon, may occur even during administration.

Additionally, some of these drugs may have unwanted side effects. In 1990, when the Food and Drug Administration tallied the numbers of hostile acts reported in association with 329 different prescription drugs, Halcion ranked No. 1 followed by Xanax. Ideally, patients with disturbed sleep should be educated not only to the effectiveness and side effects of prescription drugs, but also to the adverse effects of stimulant pharmacologic agents: cigarette smoking, caffeinated beverages and alcohol.

The use of behavioral techniques in the treatment of insomnia is based on the premise that anxiety or heightened autonomic arousal is an etiological or maintaining factor. Behavioral methods have the additional benefits of the absence of adverse side effects and rebound effects associated with drug treatment. If heightened physiological arousal or anxiety inhibits sleep, reduction of anxiety or autonomic activity levels would logically facilitate sleep. In this regard, one of the more interested findings to come out of sleep research, is that insomniacs as a group significantly overestimate sleep latencies and underestimate total sleep and sleep efficiency. Overall assessment of sleep by the patient must depend partly on the patient's own estimate of sleep duration, which in turn depends on how long the patient takes to fall asleep and how often and for how long the patient remains awake during the night. If the patient is inaccurate in assessing these factors, then the insufficiency of the patient's sleep will, ipso facto, be exaggerated.

Following this line of reasoning, several studies suggest that relaxation, systemic desensitization, biofeedback, or other anxiety reducing procedures may be effective in the treatment of insomnia.

SUMMARY OF THE INVENTION

It is therefore an object of the invention to apply behavioral techniques to the treatment of insomnia by correcting an insomniac's overestimation of sleep latency and underestimation of total sleep and sleep efficiency.

It is another object of the invention to provide a drug-free sleep training method for the insomniac to become aware of accurate determinations of sleep onset and, therefore, total sleep time.

It is yet another object of the invention to provide a sleep training method utilizing equipment that causes minimal discomfort or distraction.

It is a further object of the invention to provide a sleep training method that is self-administrable and does not require outside assistance or monitoring.

It is a still further object of the invention to provide a system for treatment of insomnia that makes the insomniac aware of his progress over time.

These and other objects of the invention are achieved by a system according to the invention that allows an insomniac to observe and record sleep onset, sleep latency, total sleep time and sleep efficiency. First, the insomniac initiates a measuring of time on a time measuring device, such as a watch, switchable by a hand actuator when the insomniac is placed in a condition to fall asleep. The user can additionally record that time. Next, when the insomniac transitions to a sleep condition, the measuring of time is halted by the equipment of the invention. When the insomniac awakens, the insomniac observes and can record the waking time.

Awake time interval can be calculated by reading the time elapsed on the time measuring device. This interval can be recorded and represents the time between being placed in a condition to fall asleep and actually falling asleep. A sleep time interval can also be calculated by subtracting the total time that the insomniac has spent trying to get to sleep from the time interval defined by the time between being placed in a condition to fall asleep and the insomniac's final waking time.

Thus, the insomniac becomes aware of the real time he spent falling asleep after going to bed or the like and of the actual time he slept. This accurate determination and realization of initial wake time and actual sleep time assists the insomniac in overcoming his misconceptions of his sleeping behavior that perpetuates the insomnia.

The time measuring device used in the system of the invention should minimize discomfort or interference with the user's sleep. The time measuring device can, for example, be secured on an insomniac's wrist in the form of a watch which includes an internal means for initiating and halting the measuring of time connected to an external activating means for controlling the time initiation and halting means. Preferably, the external activating means will be in the form of two contacts, biased in an electrically separated position and secured to the thumb of the insomniac. Alternatively, the external activating means can be in the form of a contact secured to the thumb and a contact secured to an opposing finger of the insomniac. The contacts, when connected, activate the initiation means, for example, by connecting a watch battery electrically to the watch electronics. When separated, the contacts breaks the circuit and disrupt power to the watch electronics, thereby halting the advancing time. The resulting display or reading memorializes for the user the actual time the user spent falling asleep.

When the insomniac is placed in a position to fall asleep, the insomniac will actuate the external activating means by touching the two contacts together. When the insomniac falls asleep, the insomniac moves to a sleep condition in which the contacts are separated, and the activating means is then deactivated to halt time measuring at the sleep onset time.

Upon wakening, the insomniac can calculate the wake time interval by observing the time elapsed on the time measuring device. Because the insomniac has observed the time that the insomniac was placed in the position to fall asleep and the time that the insomniac awoke, the sleep time interval may be calculated by subtracting the wake time interval from the interval between the time that the insomniac was placed in the position to fall asleep and the time that the insomniac awoke.

The system of the invention allows the insomniac to determine exactly how much time passed between lying down or the like and the onset of sleep the night before. This value can be compared to the total time spent in bed to determine the percentage of wake time elapsed during each night. Recording the total wake time and the total time spent in bed over a period of successive nights allows an insomniac to realize his improvement over time. Such realization further reduces the anxiety that can contribute to the insomnia.

The wake time interval need not be limited to a single occurrence. The insomniac can touch the contacts together at the time of each waking occurrence throughout the night. The time measuring device can re-start time measuring, not from a "zero" time, but from the point that the device halted after the first onset of sleep. The device halts time measuring again at each subsequent onset of sleep. Accordingly, the total wake lapse time during a night can easily be calculated.

The inventive method can also be repeated for as many days as the insomniac desires, calculating daily wake time intervals, sleep time intervals and total sleep time intervals, and charting these intervals for each successive day. When the insomniac is informed of the change in each interval, the insomniac can measure sleep performance due to reduced anxiety.

Thus, the invention provides a self-administered method of sleep training that is supported by psychological principles and theories from two different fields of psychology: behavioral and paradoxical. Behavioral Psychology theories state that when a behavior is coupled or followed by an adversive stimulus, that behavior will decrease. In the system of the invention, the time an insomniac stays awake is coupled with the mildly adversive stimulus of maintaining contact between the two fingertips to improve treatment of insomnia. When the insomniac falls asleep, the adversive stimulus is removed with the separation of the fingers or other contact parts. Thus, application of stimulus response theories allow the method to reduce values for total wake time.

A theory of Paradoxical Psychology states that by pairing a second behavior which is incompatible with a first behavior one is trying to control, one gains conscious control over the originating behavior. Use of the system of the invention pairs the incompatible behavior of holding two fingertips together with the behavior of falling sleep to allow an insomniac to gain control over falling asleep. Where an insomniac has greater control over falling asleep, total sleep time increases.

Accurate recording of sleep onset, which is less than the insomniac's estimate, should significantly reduce the time for sleep onset and allow the insomniac to return to sleep quicker if the insomniac awakens during the night or early morning.

BRIEF DESCRIPTION OF THE DRAWINGS

A greater understanding of the invention and its various embodiments can be gained from a reading of the following detailed description in connection with the accompanying drawings, in which.

DETAILED DESCRIPTION OF PREFERRED EMBODIMENTS

The present invention provides a sleep training treatment for insomnia, without the use of drugs, by measuring sleep time, time necessary to fall asleep (referred to herein as wake lapse time) and sleep efficiency. Observation of these measurements corrects an insomniac's overestimation of sleep latency and an insomniac's underestimation of total sleep and sleep efficiency.

Figure 1:
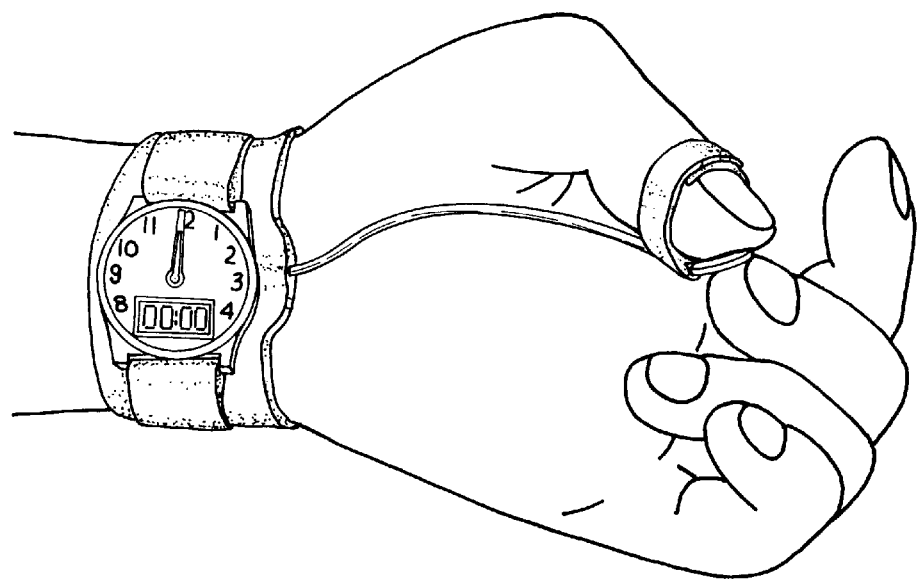
FIG. 1 is a perspective view of a preferred embodiment of the invention showing a preferred timing apparatus in a time measurement initiating position.

As shown in FIG. 1, a timing apparatus 10 of the invention includes a time measuring device and a means for initiating and halting the measuring of time. In this embodiment, the time measuring device can be in the form of a watch 12 that can have an analog face 16 or a digital display 18, or both. Also, either display can be used to record time while the other runs as a normal time-of-day clock. In another embodiment, either display 16 or 18, or both, can be used for time measuring while an external clock is used for the actual time of day. Alternatively, the time measuring device can be a table or desk clock, a wall clock, a computer, or a remote time measuring station. In general, the time measuring device can be any accurate time-keeping device that is capable of being started and stopped by the user. It is preferred that re-starting and stopping the device can be performed without having to first reset the device.

Close proximity between the time initiating and halting means and the time measuring device itself is preferred in order to minimize interference with an insomniac's ability to sleep. Accordingly, in a preferred embodiment, the invention includes attachment means such a wristband 20 for holding the watch 12 onto the insomniac's wrist. This wristband can be made of leather, plastic, or any other material capable of comfortably holding the time measuring device to the insomniac's body. Alternative embodiments for the attachment means include: a band surrounding the palm, head, or other appendage; or a removable adhesive for the skin.

Optionally, the attachment means can be eliminated to allow the time measuring device to rest a distance from the insomniac. For example, the time measuring device could be attached to the insomniac's pillow, sheet, blanket, bed frame, or any other proximate piece of furniture upon which the time measuring device may rest.

The time initiating and halting means, such as a thumb switch 14 can include of a ring 22, preferably for the thumb of the insomniac's hand, connecting means, such as wire leads 26, 27 and a touch pad switch 24.

Figure 3:
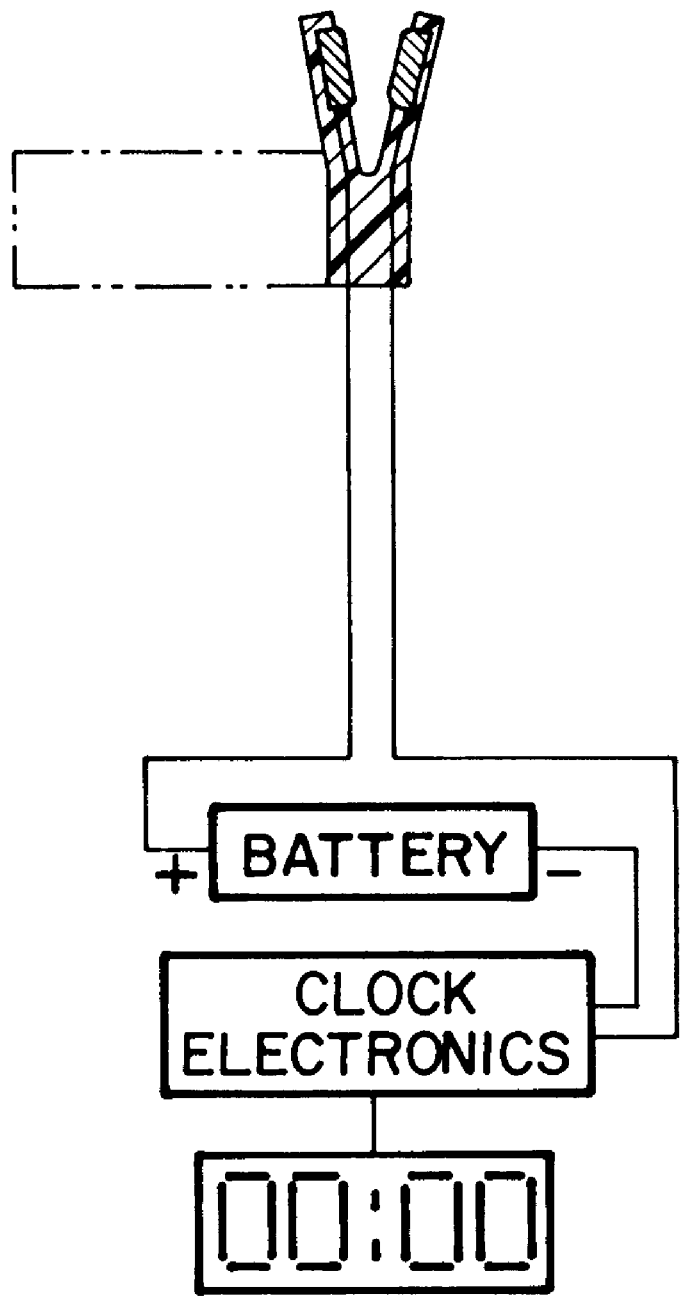
FIG. 3 is a schematic circuit diagram of FIG. 1; a preferred time apparatus of the invention.

Referring to FIG. 3, the touch pad switch 24 preferably include a non-conducting contact separation means, two electrical contacts 28 and 30 and electrically conducting wires 26 and 27. The separation means preferably comprises two metallic contact members 29a, 29b biased away from each other and spaced by an insulating spacer 29c. The contact members 29a, 29b are preferably made of an electrically conducting, light and resilient metal such as steel, and the insulating spacer 29c is preferably made of cork or plastic. The shape of the electrical contacts 28,30 can be altered in any fashion to maximize conducting contact and the number of contacts may be varied.

Referring to FIG. 1, in the preferred embodiment, when the ring is worn, the contacts 28, 30 may rest on the tip of the thumb to minimize interference with the insomniac's ability to fall asleep. Alternative embodiments of the time initiating and halting means include securing the touch pad switch 24 to some location of other appendages via elastic bands or adhering the touch pad switch 24 to some location of the insomniac's body. The two electrical contacts 28,30 can be secured to the appendage by stretching the elastic band over the appendage and placing the touch pad switch 24 in a position for actuation by an opposing finger. The placement of the touch pad switch 24 is not restricted to the insomniac's hand. Alternatively, the electrical contacts may be placed anywhere upon the insomniac's body, for example, on a toe.

Additionally, the touch pad switch 24 may be placed at a distance away from the insomniac, but nevertheless accessible to the insomniac while the insomniac is awake. For instance, the touch pad switch 24 may be placed on a nightstand or on the bed or chair where the insomniac is resting. When the user places a hand or other portion of the body on the touch pad switch 24 so as to engage the contacts, time measuring is initiated. Upon falling asleep, the insomniac will automatically remove the body part from the touch pad switch 24 and time measuring will halt.

Generally, the time initiating and halting means could comprise an easily and comfortably activated switch that, when held in a first condition by an insomniac while awake, allows the time measuring device to run. When the user insomniac falls asleep and moves to a second sleep position, the time measuring device automatically deactivates and halts time measuring, for examples by the natural separation of the fingers holding the contacts. The first condition of the switch can be either in the "on" condition or "off" condition to effect the same result. In the first instance, when the switch is held in an "on" condition by an insomniac while awake and in an "off" condition while asleep, the time measuring device 12 will have appearing on its display 16,18 at wake-up time the wake lapse time interval experienced by the insomniac during the night. On the other hand, when the switch is held in an "off" condition by an insomniac while awake and in an "on" condition while asleep, the time measuring device 12 will have appearing on its display 16,18 at wake-up time the time interval for total sleep time experienced by the insomniac during the night. Since the rest start time and wake-up time can be known by the insomniac, the total sleep time may be manually calculated for the first switch configuration and the wake lapse time may be manually calculated for the second switch configuration.

The time initiating and halting thumb switch 14 also comprises electrically conducting wires 26 running from the time measuring device to the touch pad switch 24. Preferably, the electrically conducting wires 26,27 are directly connected (hard-wired) to the time measuring device 12. Alternatively, the touch pad switch 24 alone could be secured to the insomniac, with the wires 26 running away to a remote time measuring device.

In FIG. 1, the insomniac holds the thumb and middle finger together to depress the touch pad switch 24 and engage the electrical contacts 28,30, thereby initiating measurement of time in the watch 12. In this embodiment, the two electrical contacts 28,30 remain in the engaged condition while the insomniac is awake. The watch 12 is activated, as discussed below, and begins to measure the wake lapse time before sleep.

Figure 2:
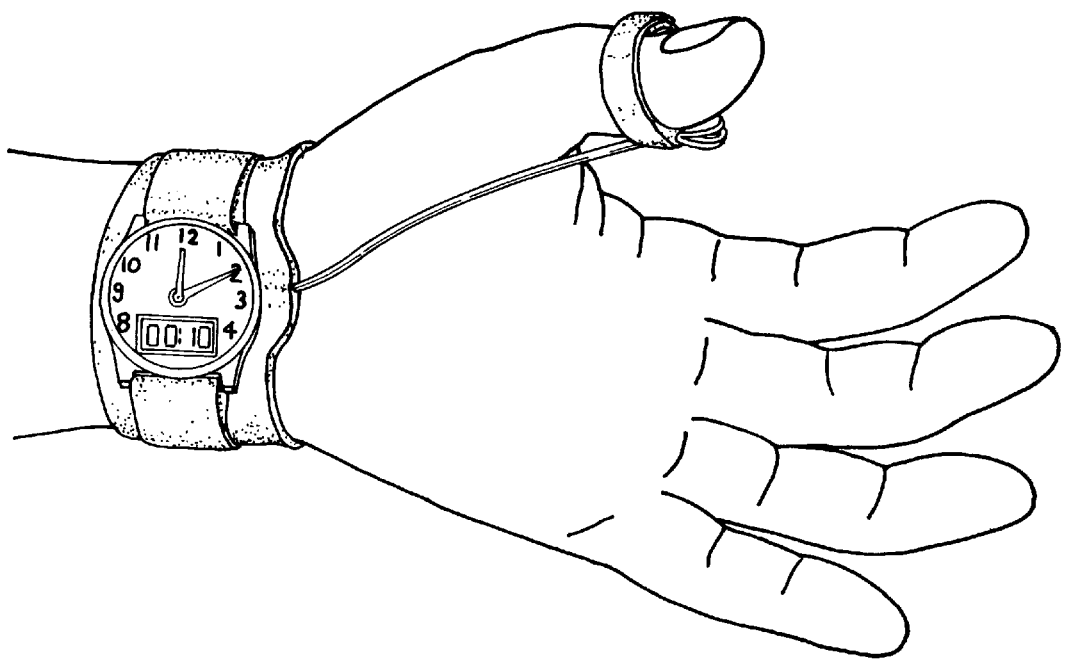
FIG. 2 is a perspective view of the embodiment of FIG. 1 in a disengaged, time measurement halting position.

As shown in FIG. 2, upon falling asleep, the thumb and middle finger of the insomniac's hand are naturally separated, and thus, the electrical contacts 28, 30, are separated. The disengagement simultaneously and automatically causes the time measuring device 12 to halt time measuring.

As can be seen on both the analog display 16 and the digital display 18 displays, the time interval for touching the electrical contacts 28, 30 together may be displayed. FIG. 1 shows the insomniac began resting at 12:00 (or 00:00 on the digital display), the system as displayed in FIG. 2 shows that the insomniac fell asleep in ten minutes, or at 12:10 (or 00:10 on the digital display). Reconnection of the electrical contacts 28,30 allows the watch 12 to continue recording the contact time beginning from the end of the first time interval, i.e. 12:10. Thus, the display, or displays 16,18 in the embodiment as shown, will read the total time interval that the electrical contacts 28,30 are connected, irrespective of the amount of disconnections between the contacts 28,30 during a given time interval.

FIG. 3 illustrates a schematic diagram of the embodiment of the timing apparatus of FIGS. 1 and 2. The electrically conducting wires 26,27 can run from the touch pad switch 24. As shown in the preferred embodiment, the first electrical contact 28 can be connected to the positive terminal 36 of the power supply 38 of the time measuring device 12; the negative terminal 40 of the power supply 38 can be connected to the negative terminal 42 of the clock's internal electronics 44; and the positive terminal 46 of the clock's internal electronics 44 may be connected to the second electrical contact 30. When an insomniac touches the two electrical contacts 28,30 together, the circuit connecting the power supply 38 to the time measuring device 12 can be completed and the clock 44 is permitted to run.

Alternatively, the initiating and halting means may be incorporated in a push button directly connected to the time measuring device, although this construction is not preferred.

Figure 4:
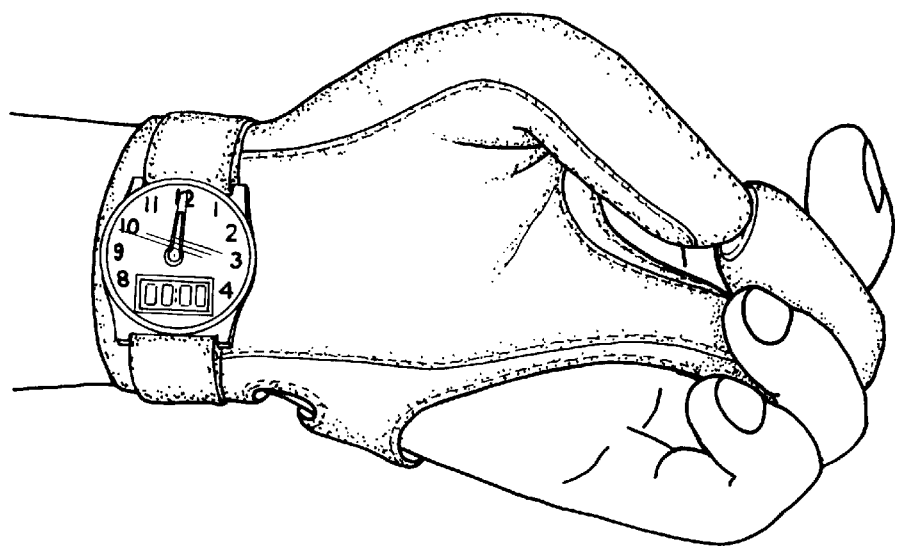
FIG. 4 is a perspective view of an alternative embodiment of the timing apparatus in a time measurement initiating position.
Figure 5:
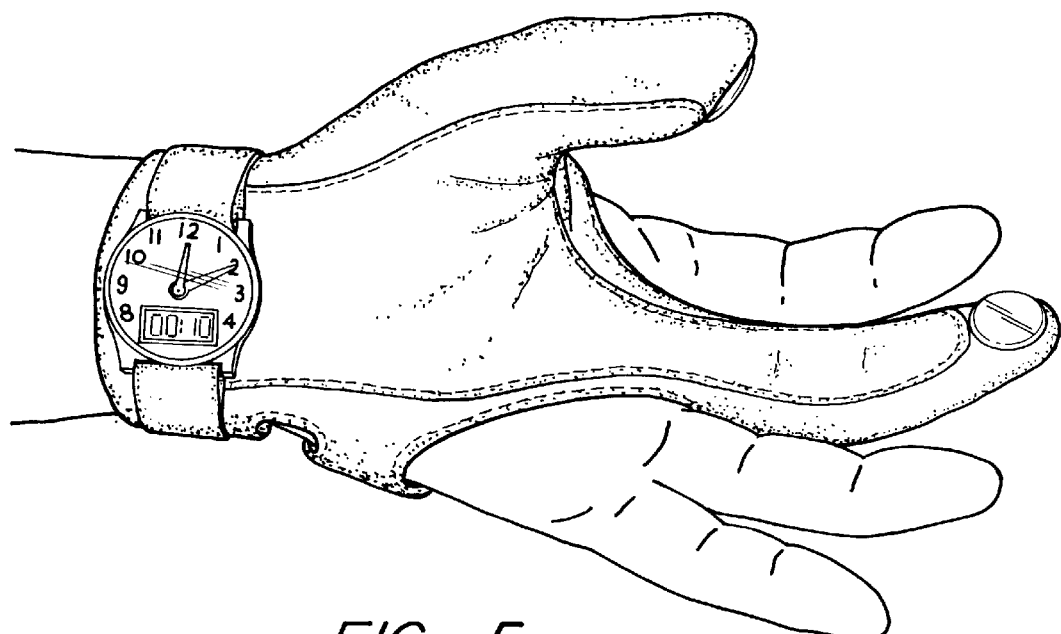
FIG. 5 is a perspective view of the timing apparatus of FIG. 4 in a disengaged, time measurement halting position.

As shown in FIGS. 4 and 5, a second embodiment 110 of the timing apparatus of the invention also includes a time measuring device and a means for initiating and halting the measuring of time. In this embodiment, the time measuring device 112 can be in the form of a watch 112 that can have an analog face 116 or a digital display 118, or both. Also, either display 116,118 can be used to record time while the other runs as a normal time-of-day clock. Both displays 16, 18 alternatively can be used for time measuring while an external clock is used for the actual time of day. Additionally, the time measuring device can be a table or desk clock, a wall clock, a computer, or a remote time measuring station.

Attachment means for holding the time measuring device onto an insomniac's wrist can include a wristband 120 which can be made of leather, velcro, or any other material capable of comfortably holding the watch 112 to the insomniac's body.

The time initiating and halting means can be made of a partial glove 122 containing two glove fingers 124,126, preferably for the thumb and middle finger of the insomniac's hand, and two electrical contacts 128,130 mounted to the respective fingers, preferably at the tips thereof. The electrical contacts 128,130 can preferably be disk-shaped and made of a light, conductive, disk-shaped metal such as steel, and the shape can be altered in any fashion to conform to the contours upon which the contacts rest. The contact 130 and glove finger 126 are preferably constructed for the middle finger but can be placed on any of the fingers opposing the thumb.

When the glove is worn, the contacts 128,130 may rest on the fingertips of the respective fingers to minimize interference with the insomniac's sleep. Alternatively, the electrical contacts 128,130 may be placed anywhere upon the insomniac's body, for example, on the two largest toes.

The time initiating and halting means also comprises electrically conducting wires 132, 134 running from the time measuring device to electrical contacts 128,130. Preferably, the electrically conducting wires are directly connected (hard-wired) to the time measuring device 112 and run within the material of the partial glove 122. Alternatively, the wires may run on the inside or outside of the glove 122. Alternatively, the wires can be secured only to the electrical contacts and run away from the insomniac to a remote time measuring device.

In FIG. 4, the insomniac holds the thumb and middle finger together to touch the two electrical contacts 128,130, thereby initiating measurement of time in the time measuring device 112 upon achieving a resting position, such as lying in a bed or otherwise positioning to go to sleep. In this embodiment, the two electrical contacts 128,130 remain in the connected condition while the user is awake.

As shown in FIG. 5, the thumb and middle finger of the insomniac's hand, and thus the electrical contacts 128,130, are separated naturally when the insomniac goes to sleep. This separation simultaneously causes the time measuring device 112 to halt time measuring.

As can be seen on both the analog display 116 and digital display 118, the time interval for touching the electrical contacts together may be displayed. Where the insomniac began resting at 12:00, the system as displayed in FIG. 5 shows that the insomniac fell asleep in ten minutes, or at 12:10. Re-initiation of electrical contact 128,130 connection allows the time measuring device 112 to continue recording the contact time beginning from the end of the first time interval, i.e. 12:10. Thus, the display, or displays 116,118 in the embodiment as shown, will indicate the total time interval that the electrical contacts 128,130 are connected, irrespective of the amount of disconnections between the contacts 128,130 during a given time interval.

Figures 6, 7:
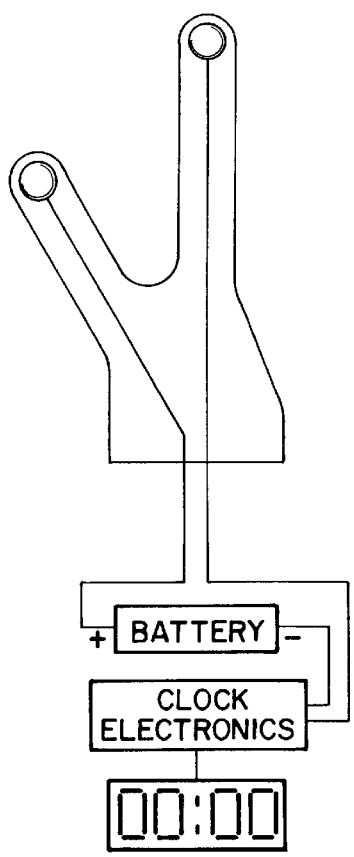
FIG. 6 is a schematic circuit for the timing apparatus of FIGS. 4 and 5.
FIG. 7 is a progress graph for use in the method according to the invention.

FIG. 6 illustrates a schematic diagram of the embodiment of the timing apparatus of FIGS. 4 and 5. The electrically conducting wires 132,134 can run from the two electrical contacts 128,130. The thumb electrical contact 128 can be connected to the positive terminal 136 of the power supply 138 of the watch 112; the negative terminal 140 of the power supply 138 can be connected to the negative terminal 142 of the clock's internal electronics 144; and the positive terminal 146 of the clock's internal electronics 144 may be connected to the middle finger electrical contact 130. When the insomniac touches the two electrical contacts 128,130 together, the circuit connecting the power supply 138 to the time measuring device 112 can be completed and the clock 144 runs.

The method and apparatus of the invention can be used over successive nights, and the results can be recorded to track improvements. As shown in FIG. 7, a chart 147 can be used to facilitate the method for aiding the treatment of sleeping disorders that are aggravated by an insomniac's underestimation of total sleep time and sleep efficiency and overestimation of time necessary to fall asleep by allowing the insomniac to graph various instances and intervals of time throughout each night and to track that time over multiple nights.

For each day of using the method, the insomniac should first record the day's date. When the insomniac is placed in a first resting position, a rest start time may be observed and recorded. The resting position can include lying down on a bed or other similar piece of furniture or sitting in a comfortable chair. Generally, the resting position can be any position that places the insomniac in a restful condition for sleep. The insomniac concurrently initiates a measuring of time in the invention's timing apparatus. In the embodiment of FIG. 1, initiating the measurement of time can be accomplished by depressing the touch pad switch 24.

The insomniac then attempts to fall asleep. At the onset of sleep, the insomniac moves to a second sleep condition that causes the measuring of time to be halted by a separation of the contacts. Thus, a wake lapse time between the initiating of time measuring and the halting of time measuring is automatically established and shown on the display(s) 16,18 of the invention's timing apparatus 12. This corresponds to the time that it has taken the insomniac to fall asleep.

The second sleep position generally can be that position an insomniac maintains at the onset of sleep, and which permits the electrical contacts 28, 30 of the preferred timing apparatus to be separated. As shown in the embodiment of FIG. 5, the second sleep condition also can be a separation of the contacts 128,130 of the thumb and middle fingers, respectively.

When the insomniac awakes, a wake-up time can be observed and recorded. The total time asleep may then be calculated by subtracting the wake lapse time from the difference between the rest start time and the wake-up time. The total sleep time can also be recorded, such as on the chart of FIG. 7.

Therefore, for each day, an insomniac may determine the time at which the insomniac fell asleep (sleep start time), the total time asleep during the night (total sleep time) and the total time awake during the night (wake lapse time).

The following example is shown to illustrate the applied method. On Jan. 1, 1995, the insomniac lies down for sleep at 12:00 midnight. The insomniac simultaneously records the rest start time as 12:00 am and initiates time measurement by touching the two electrical contacts 28,30 together. At 12:50 am, the insomniac falls asleep. The insomniac's fingers separate and the electrical contacts 28, 30 disconnect. Thus, the display(s) on the time measuring device indicate fifty (0:50) minutes, representing the wake lapse time. The insomniac wakes up at 8:00 am and records 8:00 am as the wake-up time.

Looking at the display(s) of the time measuring device, the insomniac reads the wake lapse time of fifty (0:50) minutes and records this value in the chart. Finally, the insomniac calculates a total sleep time of seven hours and ten minutes (7:10) by subtracting the wake lapse time (0:50) from the difference between the wake-up time (8:00) and the rest start time (12:00).

If the insomniac awakes more than once during the night, the above calculations are still used. The insomniac can re-initiate time measuring immediately upon each waking occurrence and, upon each subsequent falling asleep, the insomniac will move to the second sleep position, thus automatically halting the measuring of time in the invention's timing apparatus. Therefore, the time period that can be observed on the readout display of the timing apparatus at the end of the night can be the sum total of all wake time intervals throughout the entire night.

The following example is shown to illustrate the applied method with multiple waking occurrences. On Jan. 2, 1995, the insomniac lies down for sleep at 12:00 midnight. The insomniac simultaneously records the rest start time as 12:00 am and initiates time measurement by touching the two electrical contacts together. At 12:30 am, the insomniac falls asleep, the insomniac's fingers separate and the electrical contacts disconnect. The time measuring device's display(s) reads 30 minutes. Thus, at that point in time, the wake lapse time is 30 minutes. However, the insomniac awakes at 2:30 am. According to the method, the insomniac re-initiates time measurement by touching the two electrical contacts 28,30 together. When the insomniac falls asleep at 3:00 am, the fingers separate, the electrical contacts 28,30 disconnect and time measurement is again halted. The wake lapse time is therefore one hour and reads accordingly on the display. This process is repeated when the insomniac awakes at 4:00 am and falls asleep at 4:15 am. The insomniac wakes up at 8:00 am and records 8:00 am as the wake-up time.

Looking at the display(s) of the time measuring device 12, the insomniac reads the wake lapse time of one hour and fifteen minutes (1:15) and records this value in the chart. Finally, the insomniac calculates a total sleep time of six hours and forty five minutes (6:45) by subtracting the wake lapse time (1:15) from the difference between the wake-up time (8:00) and the rest start time (12:00). In this example, where multiple wakings occur during the night, a sleep start time cannot be calculated.

The steps as outlined above may be repeated over a period of nights at the insomniac's choosing. Where all of the above time instances and intervals are recorded over a period of days, weeks, months, or years, the insomniac can track average or increased performance of total time asleep during the night, and wake lapse time. If, for example, the insomniac recorded wake lapse times for a week as follows:

Monday—1:25
Tuesday—1:15
Wednesday—1:05
Thursday—0:55
Friday—0:45
Saturday—0:35
Sunday—0:25 then the insomniac would realize a positive performance result for application of the invention.

Therefore, the invention provides an insomniac with an economical, self-administered, comfortable apparatus for treating an insomniac's overestimation of sleep latency and underestimation of total sleep and sleep efficiency. The invention furnishes an insomniac with a drug-free sleep training method that allows accurate determinations of wake time during each night, and, therefore, total sleep time over a period of days or weeks, or even longer.

While specific embodiments of the invention have been set forth with a relatively high degree of particularity, it is intended that the scope of the invention not be so limited. Instead, the proper scope of the invention may include alternatives which are now within the purview of one skilled in the art. For example, the electrical contacts optionally may be terminated at an external switch input jack which may be inserted into an external switch receptacle of the time measuring device. This external embodiment could be advantageous because it would allow the time measuring device to be used free from the constrains of the electrically conducting wires. For instance, where the time measuring device is a watch, the wires could be easily disconnected from the watch by pulling out the plug connected to the electrical contacts. Free from the wires the watch could be used in its ordinary time-of-day timekeeping manner. This embodiment further allows the jack to be inserted into any receptacle contained within a time measuring device, i.e., a desk clock, a wall clock, a computer, or a remote time measuring station. This would provide the insomniac with an array of different time measuring devices for application of the instant the invention. Thus, the scope should be ascertained by a reading of the claims that follow.

I claim:

1. A time recording method for a user to automatically record awake time in a rest position to assist in the treatment of sleeping disorders, said method comprising the steps of:
   said user contacting a switch;
   said user starting a timer by contacting the switch;
   said user maintaining continued user contact with the switch and recording awake time on said timer for so long as the switch is contacted; and
   said user removing user contact from the switch when the user falls asleep and thereby stopping the timer.

2. A method as recited in claim 1, wherein the rest position is resting in a chair.

3. A method as recited in claim 1, wherein the rest position is lying down.

4. A method as recited in claim 1, further comprising the step of placing the switch between a finger and another surface.

5. A method as recited in claim 1, further comprising the step of placing the switch between a finger and a thumb.

6. A method as recited in claim 1, further comprising the step of mounting the timer to the user.

7. A method as recited in claim 1, further comprising the steps of:
   said user contacting the switch upon awakening to record further awake time with the timer; and
   said user removing user contact from the switch to stop the timer upon falling asleep again.

8. A time recording method for a user to automatically record sleep in a rest position time to assist in the treatment of sleeping disorders, said method comprising the steps of:
   said user contacting a switch to control a timer;
   said user maintaining continued user contact with said switch and preventing the recordal of time on said timer for so long as said continued contact is maintained;
   said user removing user contact from the switch when the user falls asleep and thereby starting starting the recordal of time on the timer upon falling asleep; and
   said user recording sleep time on said timer for so long as the switch is released.

9. A method as recited in claim 8, wherein the rest position is resting in a chair.

10. A method as recited in claim 8, wherein the rest position is lying down.

11. A method as recited in claim 8, further comprising the step of placing the switch between a finger and another surface.

12. A method as recited in claim 8, further comprising the step of placing the switch between a finger and a thumb.

13. A method as recited in claim 8, further comprising the step of mounting the timer to the user.

14. A method as recited in claim 8, further comprising the steps of:
   said user contacting the switch upon awakening to record further awake time with the timer; and
   said user removing user contact from the switch to stop the timer upon falling asleep again.

15. A time recording method for a user to automatically record awake time in a rest position to assist in the treatment of sleeping disorders, said method comprising the steps of:
   said user contacting a switch;
   said user starting a timer by contacting the switch;
   said user maintaining continued user contact with the switch and recording awake time on said timer for so long as the switch is contacted;
   said user falling asleep; and
   said user removing user contact from the switch when the user falls asleep and thereby stopping the timer.

16. A time recording method for a user to automatically record sleep in a rest position time to assist in the treatment of sleeping disorders, said method comprising the steps of:
   said user contacting a switch to control a timer;
   said user maintaining continued user contact with said switch and preventing the recordal of time on said timer for so long as said continued contact is maintained;
   said user removing user contact from the switch when the user falls asleep and thereby starting the recordal of time on the timer upon falling asleep; and
   said user recording sleep time on said timer for so long as the switch is released.

17. A time recording method for a user to automatically record awake time in a rest position to assist in the treatment of sleeping disorders, said method comprising the steps of:
   providing a timer activated to start and stop timing by a switch;
   said user positioning and contacting the switch between a finger and thumb of the user;
   said user starting the timer by contacting the switch;
   said user maintaining continued user contact with the switch and recording awake time on said timer for so long as the switch is contacted;

said user removing user contact from the switch When the user falls asleep and thereby stopping the timer;

attaching the timer and the switch to the user to maintain connection of the switch and the timer to the user, independent of positioning of the hand or fingers of the user.

18. A time recording method for a user to automatically record sleep in a rest position time to assist in the treatment of sleeping disorders, said method comprising the steps of:

providing a timer activated to start and stop timing by a switch;

said user positioning and contacting the switch between a finger and thumb of the user to control the timer;

said user maintaining continued user contact with said switch and preventing the recordal of time on said timer for so long as said continued contact is maintained;

said user removing user contact from the switch when the user falls asleep and thereby starting the recordal of time on the timer upon falling asleep;

said user recording sleep time on said timer for so long as the switch is released; and attaching the timer and the switch to the user to maintain connection of the switch and the timer to the user, independent of positioning of the hand or fingers of the user.

* * * * *